(12) United States Patent
Gill

(10) Patent No.: US 6,663,568 B1
(45) Date of Patent: Dec. 16, 2003

(54) ULTRASOUND TECHNIQUES

(75) Inventor: Robert Wyatt Gill, Rozelle (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/623,879

(22) PCT Filed: Mar. 11, 1999

(86) PCT No.: PCT/AU99/00157
§ 371 (c)(1),
(2), (4) Date: Nov. 15, 2000

(87) PCT Pub. No.: WO99/45839
PCT Pub. Date: Sep. 16, 1999

(30) Foreign Application Priority Data

Mar. 11, 1998 (AU) .............................................. PP2278

(51) Int. Cl.⁷ ............................................... A61B 8/06
(52) U.S. Cl. ....................... 600/456; 600/454; 600/465
(58) Field of Search ................ 600/437, 454, 600/455, 441, 456, 465

(56) References Cited

U.S. PATENT DOCUMENTS

| | | | |
|---|---|---|---|
| 4,103,679 A | | 8/1978 | Aronson ................ 128/2.05 F |
| 5,540,230 A | | 7/1996 | Vilkomerson .......... 188/662.04 |
| 5,603,323 A | * | 2/1997 | Pflugrath et al. ........... 600/437 |
| 5,609,155 A | * | 3/1997 | Guracar ...................... 600/453 |
| 5,623,930 A | * | 4/1997 | Wright et al. ............... 600/456 |
| 5,701,898 A | * | 12/1997 | Adam et al. ................ 600/454 |
| 5,844,140 A | * | 12/1998 | Seale .......................... 73/633 |
| 5,967,987 A | * | 10/1999 | Sumanaweera et al. ..... 600/454 |
| 6,071,242 A | * | 6/2000 | Lin ............................. 600/456 |
| 6,142,944 A | * | 11/2000 | Li et al. ..................... 600/453 |

OTHER PUBLICATIONS

Derwent Abstract Accession No. 96–182532/19, JP 08–056945 (Yokogawa Medical Systems Ltd.) Mar. 5, 1996.

* cited by examiner

*Primary Examiner*—Francis J. Jaworski
*Assistant Examiner*—William C. Jung
(74) *Attorney, Agent, or Firm*—Foley & Lardner

(57) ABSTRACT

A method of estimating the volume flow in a vessel utilizing ultrasound techniques including the steps of imaging the vessel utilizing an ultrasonic transducer array so as to produce fluid velocity information for the vessel, the plane formed by the beams emitted by the transducers having a direction which is offset from an axis of the vessel such that the beam plane forms an elliptical section within the vessel, and utilizing the velocity information for points within the vessel and the elliptical section to calculate a mean velocity for the fluid flow through the elliptical section. The improvement of the volume flow estimation is achieved by utilizing average velocity information and Doppler signal power, and mean velocity calculation based on a weighted summation of the velocity values a multiple measurement points with weighting factors determined by the Doppler signal power at the measurement points.

11 Claims, 5 Drawing Sheets

TRANSDUCER IS THEN ROTATED BY BETA DEGREES AROUND THE X'-AXIS

TRANSDUCER SCANNING PLANE IN THE z"-y" PLANE

VESSEL AXIS ALONG THE y-AXIS

ULTRASOUND TECHNIQUES

FIELD OF THE INVENTION

The present invention relates to the field of ultrasound imaging and, in particular, to the utilisation of ultrasound data for producing volume flow information.

BACKGROUND OF THE INVENTION

In recent years, ultrasound imaging has become increasingly important, especially in the area of medical imaging of the internal portions of a person or animal's anatomy. The principles of ultrasound imaging are well known. However, recently the utilisation of phase data from an ultrasound signal has resulted in the production of flow information associated with an ultrasound scan. A number of manufacturers now offer "Colour Doppler Imaging" which provides information in the form of colour indicators showing the direction and speed of flow of blood within vessels.

It would be desirable to provide for non-invasive real time ultrasonic measurement of the blood volume flow rate in blood vessels with a high accuracy and high degree of robustness ideally utilizing standard hardware available with only software modification.

SUMMARY OF THE INVENTION

It is an object of the present invention to provide for the accurate measurement of flow volume within the vessels utilising ultrasound techniques.

In accordance with a first aspect of the present invention, there is provided a method of estimating the volume flow in a vessel utilising ultrasound techniques, the method comprising the steps of imaging the vessel utilising an ultrasonic transducer array so as to produce fluid velocity information for the vessel, the plane formed by the beams emitted by the transducers having a direction which is offset from the axis of the vessel such that the it forms an elliptical section within the vessel; and utilising the velocity information for points within the vessel and the elliptical section to calculate a mean velocity for the fluid flow through the elliptical section.

Preferably, the mean velocity is calculated using a power weighted average of the velocity information, the power weighting being correlated to the intensity of the received signal at each point corresponding to the velocity information.

Preferably, the method further comprises the step of fitting an elliptical section to the fluid velocity information and determining the elliptical section parameters for the vessel from the fitted elliptical section.

The method is ideally suited to use on the internal portion of a human or animal's anatomy and can be implemented on a standard ultrasound machine by reprogramming of the software of the machine.

BRIEF DESCRIPTION OF THE DRAWINGS

Notwithstanding any other forms which may fall within the scope of the present invention, preferred forms of the invention will now be described, by way of example only, with reference to the accompanying drawings in which.

DESCRIPTION OF PREFERRED AND OTHER EMBODIMENTS

In the preferred embodiment, an oblique scan method is utilised to extract the details of an elliptical cross sectional structure of a vessel and to utilise the elliptical structure, in conjunction with fluid movement information within the cross sectional structure, so as to derive a volume flow.

Figure 1:
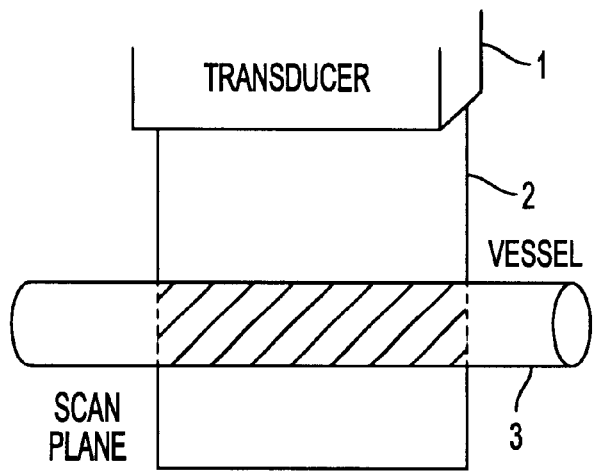
FIG. 1 illustrates the standard longitudinal scan process.

Turning initially to FIG. 1, there is illustrated a schematic of the normal ultrasound processing technique. The normal arrangement includes a transducer 1 which can include an array of transmitters and receivers arranged in a line. The transducer 1 emits a beam 2 which is of a substantially planar form having a predetermined thickness. The beam 2 is projected through a vessel 3 with reflections being received back to the transducer 1 and subsequently processed so as to determine the structure of the vessel. In Colour Doppler Imaging, a series of emissions are made in a periodic manner in rapid succession and the return reflections recorded. The phase difference between multiple returns is determined and utilised to calculate flow velocity information within the vessel 3 in a known manner.

Figure 2:
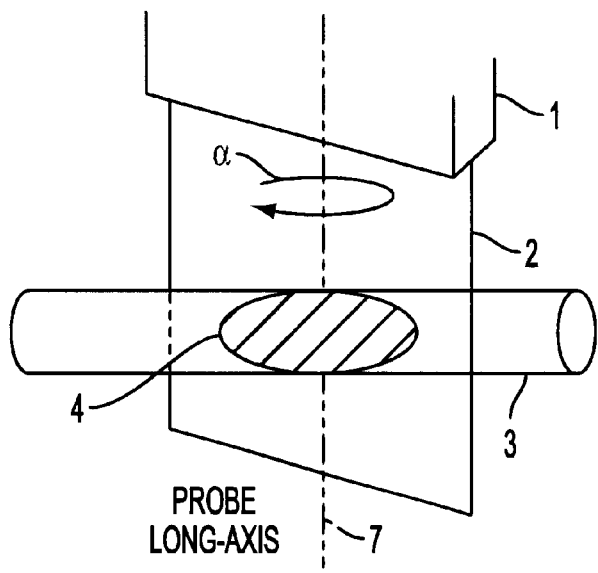
FIG. 2 illustrates a first rotation of the scan plane relative to a vessel.
Figure 3:
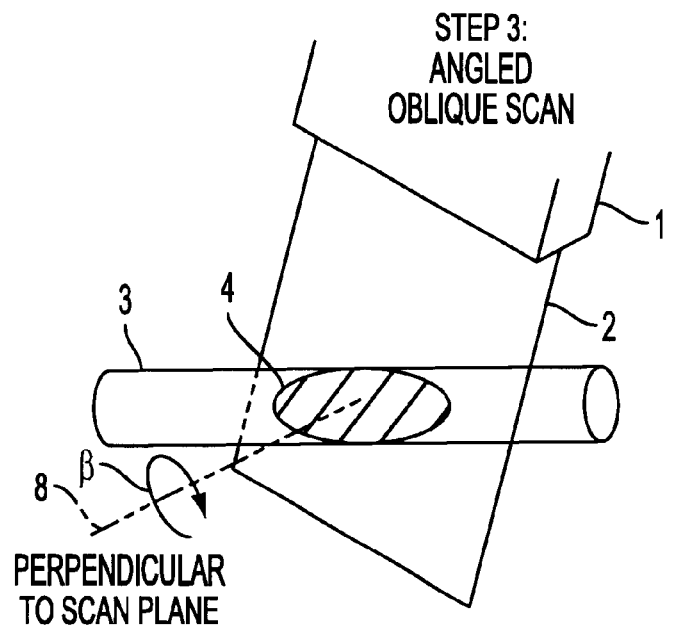
FIG. 3 illustrates a second rotation of the scan plane relative to a measured vessel.

In the preferred embodiment, an oblique scan is utilised where the orientation of the beam 21 does not line up with the vessel 3. In particular, as illustrated in FIGS. 2 and 3, two forms of oblique scan beam rotation are provided. Firstly, as shown in FIG. 2 a rotation α of the transducer probe about an axis 7 that is perpendicular to the vessel longitudinal axis (ie. about the probe longitudinal axis) is utilised resulting in a first cross sectional volume 4. Secondly, as illustrated in FIG. 3, a rotation β around an axis 8 perpendicular to the scan plane is provided. This results in a final cross section 4 of the vessel 3 taking an elliptical sectional form being of a predetermined volume which is determined by the thickness characteristics of the transducer beam.

In the preferred embodiment a sequence of frames is imaged utilising the angled oblique scan of FIG. 2 and FIG. 3 and subsequently processed as discussed hereinafter to determine an actual volume flow rate through a vessel of interest.

Figure 8:
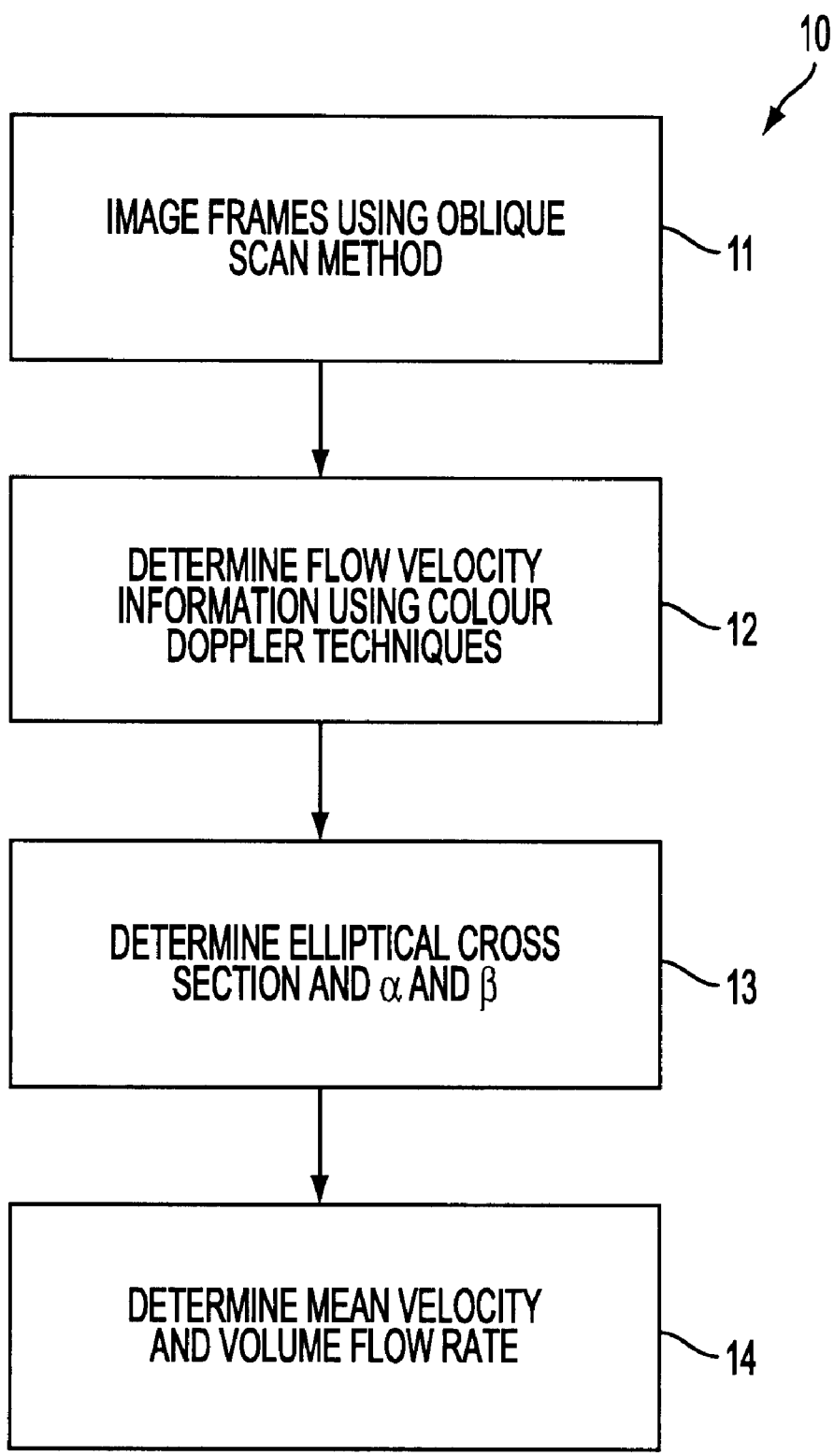
FIG. 8 illustrates the steps in the preferred embodiment.

Turning now to FIG. 8, there is illustrated the steps 10 in the method of the preferred embodiment. The method proceeds 11 by initially utilizing standard modern ultrasound equipment to capture a series of frames using an oblique scan method.

From the captured sequence of frames, corresponding velocity information is obtained 12 utilising the known Colour Doppler techniques, the method of obtaining the colour flow data being entirely standard.

Next, the colour flow images are examined so as to identify an elliptical cross section and from this, the geometric parameters of the scan (α and β) are obtained 13. The ratio of the ellipsoid minor to major axes is utilised to calculate the angle α whilst the orientation of the major axis relative to the horizontal in the scan and the colour Doppler steering angle can be used to determine β.

Once the overall elliptical structure has been determined, it is subsequently utilised to compute the cross sectional area of the vessel. Subsequently, with the knowledge of the geometry and the mean velocity, a volume, flow rate estimate can be calculated 14.

A more detailed understanding of the process can be gained by examining the steps used to mathematically simulate the scanning and signal processing.

In order to determine and identify the ellipse parameters and to calculate the flow volume, the image plane received by the transducer element is scanned sequentially and for each scan coordinate, the corresponding vessel coordinate is obtained for processing so as to determine whether the sample coordinate (which represents a sample voxel) is within the vessel lumen or otherwise.

Figure 4:
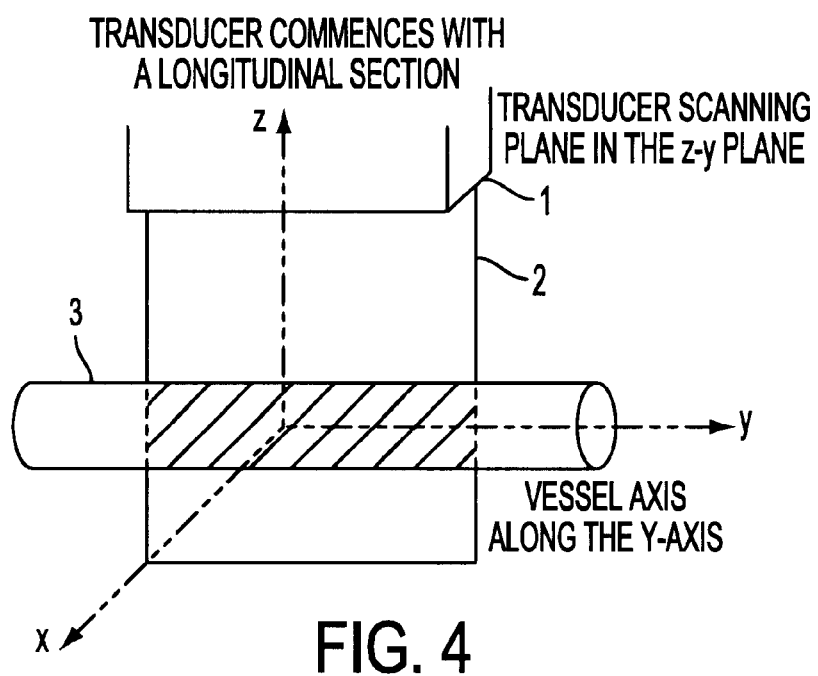
FIGS. 4–6 illustrate the process of coordinate transforms utilised in the preferred embodiment.

It is therefore necessary to transform between the scan plane coordinate space and the vessel coordinate space. The transformation process will now be discussed with reference to FIGS. 4 to 6. In FIG. 4, there is illustrated an x, y, z coordinate system of the vessel. FIG. 4 also shows the transducer 1 aligned in the z–y plane. In the angle oblique scan process the vessel coordinates remain in the x, y, z, frame of reference whilst the scanning plane coordinates are transformed into x", y", z" frame of reference utilising two rotations.

Figure 5:
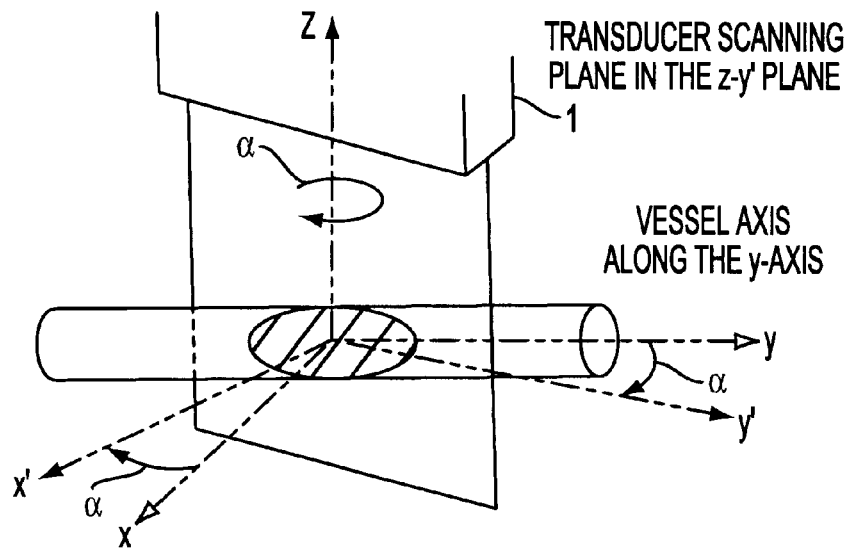

As shown in FIG. 5, the first rotation is a rotation of the transducer 1 by α degrees around the z axis as illustrated in FIG. 5. Utilising a matrix notation, we can write this translation as:

$$\begin{bmatrix} x' \\ y' \\ z' \end{bmatrix} = \begin{bmatrix} \cos L(x, x') & \cos L(y, x') & \cos L(z, x') \\ \cos L(x, y') & \cos L(y, y') & \cos L(z, y') \\ \cos L(x, z') & \cos L(y, z') & \cos L(z, z') \end{bmatrix} \begin{bmatrix} x \\ y \\ z \end{bmatrix} \quad (1)$$

Using the nomenclature from FIG. 5, the direction cosines are as follows:

$$\begin{bmatrix} x' \\ y' \\ z' \end{bmatrix} = \begin{bmatrix} \cos(\alpha) & \cos(\pi/2+\alpha) & \cos(\pi/2) \\ \cos(\pi/2-\alpha) & \cos(\alpha) & \cos(\pi/2) \\ \cos(\pi/2) & \cos(\pi/2) & \cos(0) \end{bmatrix} \begin{bmatrix} x \\ y \\ z \end{bmatrix} \quad (2)$$

ie.

$$\begin{bmatrix} x' \\ y' \\ z' \end{bmatrix} = \begin{bmatrix} \cos(\alpha) & -\sin(\alpha) & 0 \\ \sin(\alpha) & \cos(\alpha) & 0 \\ 0 & 0 & 1 \end{bmatrix} \begin{bmatrix} x \\ y \\ z \end{bmatrix} \quad (3)$$

Figure 6:
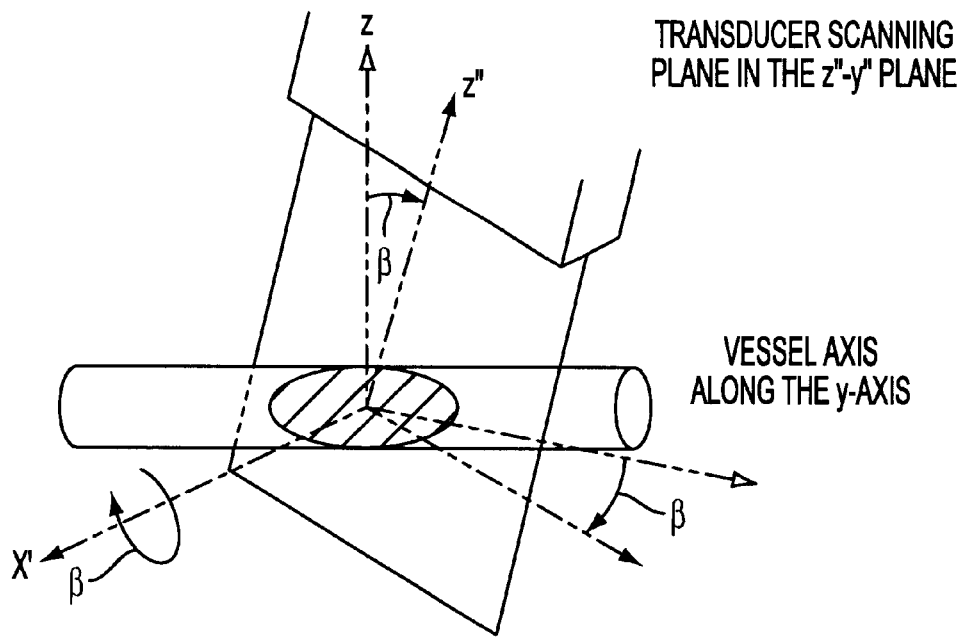

In the second transformation illustrated in FIG. 6, we go from the x'–y'–z' frame of reference to the x"–y"–z" frame of reference through the rotation of the transducer by β degrees. The transformation is expressed as follows:

$$\begin{bmatrix} x'' \\ y'' \\ z'' \end{bmatrix} = \begin{bmatrix} \cos L(x', x'') & \cos L(y', x'') & \cos L(z', x'') \\ \cos L(x', y'') & \cos L(y', y'') & \cos L(z', y'') \\ \cos L(x', z'') & \cos L(y', z'') & \cos L(z', z'') \end{bmatrix} \begin{bmatrix} x' \\ y' \\ z' \end{bmatrix} \quad (4)$$

Using the nomenclature illustrated in FIG. 6 for the direction cosines, one obtains:

$$\begin{bmatrix} x'' \\ y'' \\ z'' \end{bmatrix} = \begin{bmatrix} \cos(0) & \cos(\pi/2) & \cos(\pi/2) \\ \cos(\pi/2) & \cos(\beta) & \cos(\pi/2+\beta) \\ \cos(\pi/2) & \cos(\pi/2-\beta) & \cos(\beta) \end{bmatrix} \begin{bmatrix} x' \\ y' \\ z' \end{bmatrix} \quad (5)$$

ie.

$$\begin{bmatrix} x'' \\ y'' \\ z'' \end{bmatrix} = \begin{bmatrix} 1 & 0 & 0 \\ 0 & \cos(\beta) & -\sin(\beta) \\ 0 & +\sin(\beta) & \cos(\beta) \end{bmatrix} \begin{bmatrix} x' \\ y' \\ z' \end{bmatrix} \quad (6)$$

From equations (3) and (6), it is possible to combine the transformations to obtain a single transformation from z–y–z to x"–y"–z":

$$\begin{bmatrix} x'' \\ y'' \\ z'' \end{bmatrix} = \begin{bmatrix} 1 & 0 & 0 \\ 0 & \cos(\beta) & -\sin(\beta) \\ 0 & \sin(\beta) & \cos(\beta) \end{bmatrix} \begin{bmatrix} \cos(\alpha) & -\sin(\alpha) & 0 \\ \sin(\alpha) & \cos(\alpha) & 0 \\ 0 & 0 & 1 \end{bmatrix} \begin{bmatrix} x \\ y \\ z \end{bmatrix} \quad (7)$$

which gives:

$$\begin{bmatrix} x'' \\ y'' \\ z'' \end{bmatrix} = \begin{bmatrix} \cos(\alpha) & -\sin(\alpha) & 0 \\ \cos(\beta)\sin(\alpha) & \cos(\beta)\cos(\alpha) & -\sin(\beta) \\ \sin(\beta)\sin(\alpha) & \sin(\beta)\cos(\alpha) & \cos(\beta) \end{bmatrix} \begin{bmatrix} x \\ y \\ z \end{bmatrix} \quad (8)$$

or, through matrix inversion, $$\begin{bmatrix} x \\ y \\ z \end{bmatrix} = \begin{bmatrix} \cos(\alpha) & \cos(\beta)\sin(\alpha) & \sin(\beta)\sin(\alpha) \\ -\sin(\alpha) & \cos(\beta)\cos(\alpha) & \sin(\beta)\cos(\alpha) \\ 0 & -\sin(\beta) & \cos(\beta) \end{bmatrix} \begin{bmatrix} x'' \\ y'' \\ z'' \end{bmatrix} \quad (9)$$

Interestingly, the matrices in equations (8) and (9) are the transposes of one another.

In the "idealised" simulation, the position of the sample volume (0,y",z") is incremented through the extent of the scan-plane and the corresponding vessel coordinates (x,y,z) calculated using equation (9). If the sample volume lies within the vessel lumen (ie, if $\sqrt{x^2-z^2}$<Radius) then a corresponding power value is assigned a value of 1.0 and the velocity assigned a value based on a radial distance from the vessel axis.

Unfortunately, the aforementioned analysis ignores the fact the transducer beam has a finite width and is likely to have an approximately Gaussian intensity cross section. Hence, it is highly desirable to include the ultrasound parameters in the calculation of both power and velocity values for each sample volume or voxel location.

Geometry Determination (Ellipse Fitting) (Step 13 of FIG. 8)

The first step in this process is determination of the geometry, which requires the fitting of an ellipse to the power or velocity data. The data utilised to fit the ellipse can include a combination of the power data, the velocity data and the grey scale information. In one example, the power data is utilized to fit the ellipse, suppressing power values below a threshold value and suppressing areas having significant grey scale values.

The algorithm used for ellipse fitting is based on a moment of inertia formula. For velocity data, only values above a specified velocity threshold are used and each value carries equal weight in the calculation of the moment of inertia. On the other hand, when fitting an ellipse to power data, values above the specified power threshold may be taken as weights in calculating the moment of inertia. Thus, higher power regions may contribute more to the calculation than lower power areas.

Having fitting the ellipse, the angles $\alpha$ and $\beta$ are calculated as follows:

$$\alpha = \sin^{-1}(b/a) \quad (12)$$

where a=length of major axis of ellipse and b=length of minor axis of ellipse =diameter of vessel $\beta$=angle between the major axis of the ellipse and the horizontal in the scan.

Figure 7:
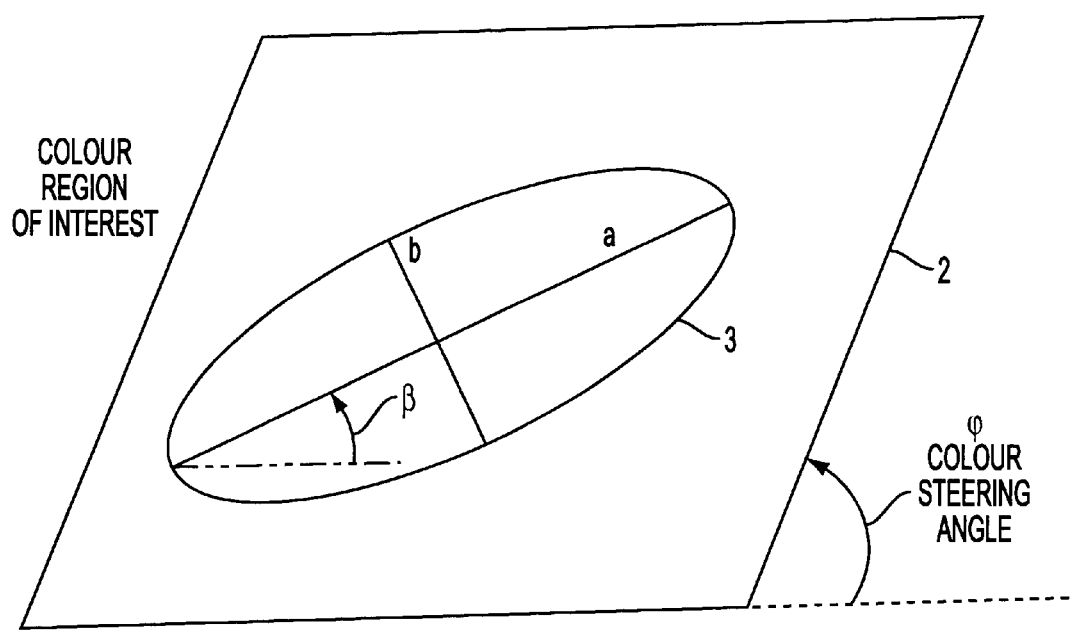
FIG. 7 illustrates the relationship between variables utilised in the preferred embodiment.

From $\alpha$ and $\beta$, the "Doppler angle" correction can be calculated as follows:

$$\cos(\theta_{Doppler}) = \cos(\alpha)\cos(\phi-\beta)$$

where $\phi$ is the Colour Doppler steering angle which can typically be say 70°, 90° or 110° but is not limited thereto, The relationship between a,b,$\beta$, and $\phi$ is as illustrated in FIG. 7.

The true area of the cross section (perpendicular to the axis of the vessel) can be calculated using angle $\alpha$ as follows:

$$A_{actual} = A_{measured} \cdot \sin(\alpha) \quad (14)$$

Mean Velocity Calculation (Step 14 of FIG. 8)

As noted previously, once the geometric parameters have been measured from the elliptical cross section, the next step in the preferred embodiment is to compute the mean velocity over the volume bounded by the ellipse.

Preferably, a power weighted summation process as described by the following formula is used:

$$\bar{v} = \frac{\Sigma P(y'',z'') \cdot v(y'',z'')}{\Sigma P(y'',z'')}\bigg|_{(y'',x'')within\ ellipse} \quad (15)$$

where P represents the power values received and v represents the received velocity values.

This scheme gives reduced weight to voxels with lower power, for example those which are only partially within the vessel. The power-weighted approach, therefore, addresses the "partial volume" effect related to the finite voxel size.

Naturally, angle correction is necessary to obtain the true mean-velocity from the mean measured velocity. Such a correction can be applied as follows:

$$\bar{v}_{true} = \frac{\bar{v}_{measured}}{\cos(\theta_{Doppler})} \quad (16)$$

Volume Flow Rate Estimation (Step 14 of FIG. 8)

Given the geometric parameters $\alpha$, $\beta$, and measured area and the mean velocity, the volume flow rate Q can be calculated with the aid of equations (13), (14) and (16) as follows:

$$Q = \bar{v} \cdot \bar{A} = \frac{\bar{v}_{measured}}{\cos(\theta_{Doppler})} A_{actual} \quad (17)$$
$$= \frac{\bar{v}_{measured} A_{measured} \sin(\alpha)}{\cos(\alpha)\cos(\varphi-\beta)} = \frac{\bar{v}_{measured} A_{measured} \tan(\alpha)}{\cos(\varphi-\beta)}$$

It can be seen from the foregoing that with the utilisation of a power weighting system a more accurate velocity and flow volume result is provided.

Of course, many modifications are possible. One such modification would be to utilize a "predicted power weighting" of a modelled power weighting for a particular ellipsoid sectional structure. This alleviates the possible problems associated with noisy power data.

As a further modification, the positional data can be utilized to process the flow information to screen for tissue echoes etc. This modification can include the examination of the traditional grey scale data usually provided on ultrasound machine and using this information to suppress velocity data values in the area of significant tissue echoes due to their likely spurious data.

It would be appreciated by a person skilled in the art that numerous other variations and/or modifications may be made to the present invention as shown in the specific embodiments without departing from the spirit or scope of the invention as broadly described. The present embodiments are, therefore, to be considered in all respects to be illustrative and not restrictive.

I claim:

1. A method of estimating the volume flow in a vessel utilizing ultrasound techniques, said method comprising the steps of:

scanning said vessel utilizing an ultrasonic transducer to obtain average fluid velocity information and corresponding Doppler signal power values for said vessel at a plurality of measurement points on a plane, said plane having a direction which is offset from the perpendicular to the axis of said vessel such that an elliptical section is scanned within said vessel; and utilizing said average velocity information and corresponding Doppler signal power values for a plurality of said measurement points within said vessel and said elliptical section to calculate a mean velocity for said fluid through the elliptical section, said mean velocity calculation based on a weighted summation of the velocity values at said plurality of measurement points, with the weighting factors determined by the Doppler signal power at the measurement points.

2. A method as claimed in claim 1 further comprising the step of fitting an elliptical section to said fluid velocity information and determining the elliptical section parameters for said vessel from said fitted elliptical section.

3. A method as claimed in claim 2, wherein said elliptical section parameters including: a first angle $\alpha$ being a rotation angle measure that the plane formed by the beams of the transducer makes with the axis of the vessel; and a second angle $\beta$ being a rotation of the ellipse around a line perpendicular to the plane formed by the beams of the transducer.

4. A method as claimed in claim 1 wherein said vessel is formed within a human or animal's anatomy.

5. A method as claimed in claim 1 wherein said method is implemented on a standard ultrasound machine by reprogramming of the software of said machine.

6. A method as claimed in claim 1 wherein said velocity information is preprocessed so as to suppress velocity data values in areas having gray-scale echoes from said ultrasonic transducer exceeding a predetermined limit.

7. A method as claimed in claim 1 wherein said power weighted average of said fluid velocity information is calculated substantially in accordance with the formula:

$$v = \Sigma P(y,x) * v(y,z)/\Sigma P(y,z)$$

wherein P represents the receiver Doppler power value and v represents the velocity estimate at the point y,z.

8. A method as claimed in claim 1, wherein scanning said vessel forms a scanned region of substantially planar form perpendicular to the face of the ultrasonic transducer.

9. A method as claimed in claim 8, wherein the scanned region is of a predetermined thickness.

10. A method as claimed in claim 1, wherein said utilizing step comprises utilizing a power weighted average of said fluid velocity information, said power weighting average being correlated to the intensity of a received signal at a point corresponding to said fluid velocity information.

11. A method as claimed in claim 10 wherein power weighted averages less than a predetermined magnitude are discarded.

* * * * *